United States Patent [19]

Chavin et al.

[11] Patent Number: 4,614,795
[45] Date of Patent: Sep. 30, 1986

[54] DEGLYCOSYLATED HUMAN FACTOR VIII:C

[75] Inventors: Stephen I. Chavin; Philip J. Fay, both of Rochester, N.Y.

[73] Assignee: University of Rochester, Rochester, N.Y.

[21] Appl. No.: 570,728

[22] Filed: Jan. 13, 1984

Related U.S. Application Data

[63] Continuation-in-part of Ser. No. 405,456, Aug. 5, 1982, Pat. No. 4,495,175.

[51] Int. Cl.[4] .................. C07G 7/00; A61K 35/16
[52] U.S. Cl. .................. 530/383; 530/830; 424/101; 514/2; 514/802
[58] Field of Search .................. 260/112 B, 112 R; 424/101; 514/2, 802, 834

[56] References Cited

U.S. PATENT DOCUMENTS

| | | | |
|---|---|---|---|
| 4,188,318 | 2/1980 | Shanbrom | 424/101 |
| 4,278,594 | 7/1981 | Amrani | 424/101 |
| 4,361,509 | 11/1982 | Zimmerman et al. | 424/101 |
| 4,383,989 | 5/1983 | Rock | 424/101 |
| 4,495,175 | 1/1985 | Chavin et al. | 424/101 |
| 4,508,709 | 4/1985 | Amphlett et al. | 424/101 |

Primary Examiner—John Kight
Assistant Examiner—Nathan M. Nutter
Attorney, Agent, or Firm—Robert M. Hallenbeck; Martin L. LuKacher; James Gibblin

[57] ABSTRACT

Highly purified, biologically active Human Factor VIII:C having specific activities of about 4000–8000 units per milligram of protein is prepared. In the method of preparation, an AHF concentrate is solubilized or equilibrated in an aqueous medium and treated to change the effective Stokes' radius of the Factor VIII:C to an apparently low value and then subjected to a separation from the concentrate. Treatment of the highly purified Factor VIII:C with a mixture of glycosidases causes substantial removal of carbohydrate side chains without reduction of procoagulant activity and with retention of significant in vivo survival time.

2 Claims, 8 Drawing Figures

```
              EXO+
EXO    UN    ENDO
```

DEGLYCOSYLATED HUMAN FACTOR VIII:C

CROSS REFERENCE TO RELATED APPLICATION

This is a continuation-in-part of U.S. patent application Ser. No. 405,456, filed Aug. 5, 1982 now U.S. Pat. No. 4,495,175.

BACKGROUND OF THE INVENTION

1. Field of the Invention:

This invention relates to and has among its objects the provision of novel methods for the preparation of highly-purified human Factor VIII:C and of a novel procoagulant material having substantially less carbohydrate than native human Factor VIII:C.

2. Description of the Prior Art:

It is known that the clotting of human blood is a complicated process, involving a series of reactions mediated by 13 different factors. It also is well known that a cause of hemophilia is the inability of the afflicted individual to synthesize one of these factors, known variously as antihemophilic factor, AHF, AHG, Factor VIII or Factor VIII C, in amounts sufficient to support adequate clotting. Dried preparations of AHF concentrate are sold commercially for administration to hemophiliacs for treatment of bleeding or in advance of surgery. The AHF concentrate is obtained from plasma from human donors, through the use of known techniques.

The usual commercial AHF preparation is not pure Factor VIII:C. Rather, it is an AHF-enriched fraction obtained from plasma. It is desirable that the AHF concentrate be as pure as possible, but further improvements in purity through modification of the procedure for isolating AHF from plasma have not been practically feasible due to the difficulty of separating plasma components. AHF is quite difficult to separate and purify because of its low content in the plasma and the instability of its activity. The known AHF concentrates are prepared from fraction I separated from plasma by means of Cohn's ethanol fractionation method or from the cryoprecipitate obtained by freezing a plasma and then thawing it at a low temperature. However, they are all crude products of low purity and contain a large quantity of fibrinogen.

As mentioned above, the AHF concentrates obtained by the prior art processes discussed above are of relatively low specific activity, namely about one unit or less of AHF activity per milligram (mg) of protein, one of the undesirable impurities being denatured AHF. U.S. Pat. Nos. 4,289,691 and 4,302,445 disclose processes for preparing AHF preparations having a specific activity of AHF activity of 1-3 units per mg of protein, and U.S. Pat. No. 4,294,826 describes a method for preparing human AHF having a specific activity of about 1-10 units of AHF activity per mg.

AHF, or Factor VIII, is now known, however, to exist as a complex of several different protein subunits with several different functions. The exact nature of the complex (i.e. whether the subunits are separate molecules or parts of one molecule and which functions are associated with which subunits) is not yet fully understood. However, it is now known that procoagulant activity, or AHF, or antihemophiliac activity is associated with one subunit, termed Factor VIII:C. Von Willebrand activity, measured as platelet aggregation activity, is associated with a subunit termed Factor VIII:vWF or Factor VIII R:Ag. Another functional subunit is termed Factor VIII C:Ag since this subunit contains the F VIII antigen.

Several investigators have tried to separate F. VIII:C from other active Factor VIII components, as disclosed in Fulcher et al, *P.N.A.S.*, 79:1648-152 and the related patent, U.S. Pat. No. 4,361,509, cited in the copending application. Carbohydrate side chains have been studies in multimeric Factor VII:C/vWF to determine their role in platelet aggregation. In addition, alteration of these side chains is known to affect plasma clearance. These side chains are thought to terminate in sialic acid residues linked to galactosyl residues. In mammals, a specific hepatic receptor recognizes terminal galactosyl residues on glycoproteins which have been treated to remove sialic acid, so that these asialoglycoproteins are cleared rapidly by the liver.

Sodetz et al, *J. Biol. Chem.*, 252:5538-46, (1977) disclose the neuramidase treatment of human F. VIII:C/vWF purified from human AHF concentrates. They found that upon removal of sialic acid, vW (platelet aggregating) activity is markedly reduced, while procoagulant activity remains constant. The circulating half-life of the treated protein in rabbits goes from about 240 min. to about 5 min.

Sodetz et al, *J. Biol. Chem.*, 253:7202-7206, (1978) report treatment of F. VIII:vWF with neuramidase as in the previous experiment, followed by incubation with galactosidase to remove 62% of the galactose. Procoagulant activity was not decreased, but VW activity dropped markedly.

From these studies it was concluded that vWF activity is dependent on terminal sialic acid residues, the penultimate galactose residues, and protein structure.

Gralnick et al, *P.N.A.S.*, 80:2771-2774, (1983) treated F. VIII/vWF with neuramidase beta galactosidase, and galactose oxidase. They reported, consistently with Sodetz et al, that this treatment reduced vWF activity. It was suggested that the next-to-terminal galactose is responsible for maintaining the largest multimers of the factor VIII/vWF factor protein. Treatment of intact protein with these enzymes did not produce a lowering of vWF or procoagulant activity, but treatment of the asialo factor VIII/vWF protein with beta galactosidase resulted in a time-dependent decrease of vW factor activity. This was correlated with loss of the largest multimeric subunits and vW activity.

SUMMARY OF THE INVENTION

The preparations produced by the method of the invention have about 4000-8000 units of AHF (procoagulant) activity per mg of protein (one unit of activity is that found in 1 ml of normal human plasma). The product appears as homogeneous and having a molecular weight of about 95,000 on SDS/PAGE.

The present invention is directed to essentially pure human F. VIII:C, free of F. VIII:vWF and other procoagulant activities, and which is substantially reduced in carbohydrate content.

The invention is further directed to such homogeneous F. VIII:C, free of F. VIII:vWF and other procoagulant activities having less than 50% of the carbohydrate of naturally occurring human F. VIII:C. This material retains essentially all of its procoagulant activity, and retains significant survival in vivo. Its molecular weight on SDS/PAGE is approximately 95,000, compared to 100,000 for the highly purified human F.

VIII:C. This is consistent with published reports that AHF (including vWF) generally contains about 10%–15% carbohydrate. The present material, as prepared, therefore contained about 7.5% to 5% carbohydrate. It is contemplated that deglycosylated material similar to the present invention can be prepared by genetic engineering methods involving expression of the human F. VIII:C gene in systems wherein no carbohydrate is added to synthesized protein.

DESCRIPTION OF THE PREFERRED EMBODIMENTS

Figure 1:
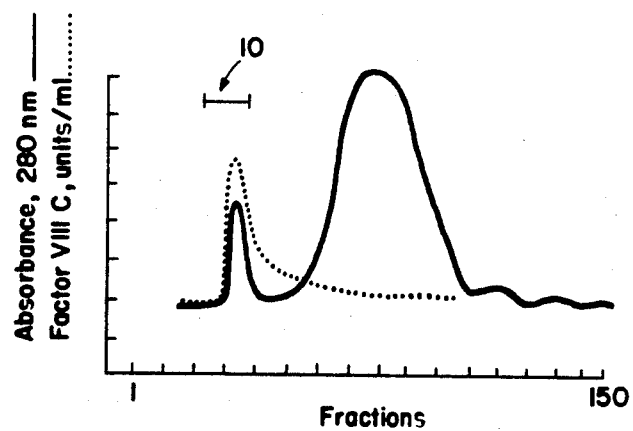
FIGS. 1–4 are depictions of the chromatographic separations of AHF (Factor VIII C) in the steps of the method of the invention.

The starting material of the present invention is a concentrate of AHF obtained from human blood plasma, such as a commercially available AHF preparation.

The concentrate of AHF is subjected to a separation on the basis of Stokes' radius wherein proteins of lower molecular weight are separated from AHF, which exhibits an apparently high Stokes' radius. The above separation may be accomplished in a variety of ways such as subjecting the AHF concentrate to gel permeation chromatography on cross-linked agarose (such as Biogel A-15 m or Sepharose CL-4B) or cross-linked polyacrylamide or to a controlled pore size glass bead treatment or to sucrose density gradient ultrafiltration. All of the above techniques are well-known in the art. Preferably, the AHF concentrate is subjected to gel permeation chromatography on, for example, cross-linked agarose or polyacrylamide. After equilibration on the chromatographic medium, AHF is eluted with a buffered salt solution having an ionic strength of about 0.1–0.4 and a pH of about 6.0–7.5.

The fractions containing the eluted AHF from above are pooled and the pool is concentrated by techniques known in the art such as precipitation with ammonium sulfate, sodium sulfate, etc., by diafiltration, by PEG addition, or the like. For example, the AHF pool may be treated with ammonium sulfate (30–40%, weight/volume) to precipitate AHF. The AHF, after concentration, is dissolved or equilibrated in an aqueous salt buffer of pH about 6.0–7.5 and ionic strength about 0.1–0.4. If a salt such as ammonium sulfate was added in the course of concentration of the AHF pool, such salt is removed prior to the next step by known techniques such as dialysis, diafiltration, and the like.

Next, the AHF concentrate is treated to change the effective Stokes' radius of the AHF molecule to an apparently low value. To this end one may add a source of divalent cations such as calcium or magnesium wherein about 5–10 parts by volume of protein solution with 1 part of a solution about 1–3M in divalent cation is employed per part by volume of AHF concentrate. The above mentioned reduction in Stokes' radius can also be accomplished by attaining a high ionic strength in solutions of AHF (e.g. about 1–4M with sodium chloride) or the incubation of AHF with about 0.01–0.001 parts of thrombin per part of AHF concentrate (in units) (Leon W. Hoyer, Hemophilia and Hemostasis, "The Factor VIII Complex:Structure & Function", Alan R. Liss, Inc., pg. 7, [1981]).

Following reduction in Stokes' radius of the AHF molecule, the AHF concentrate is treated to remove divalent cations by known procedures such as dialysis or diafiltration and then is subjected to a separation on the basis of Stokes' radius by any of the means described above. Preferably, the AHF concentrate is subjected to gel permeation chromatography on cross-linked agarose or polyacrylamide, chromatographic medium equilibrated and eluted with a buffered salt solution having an ionic strength of about 0.1–0.4 and a pH of about 6.0–7.5.

The eluted fractions containing AHF activity are pooled and optionally concentrated by reduction of water content. To this end the pooled fractions may be concentrated by techniques known in the art such as dialysis, diafiltration, etc. The fractions may be immersed in, for example, solid PEG 20,000 in order to extract water from the solution within a dialysis container. The concentrated material is treated to remove divalent cations by dialysis, diafiltration, or the like, against a buffer at a pH of about 6.0–7.5.

Following the above concentration steps, the fraction containing AHF activity is subjected to chromatography on an anion exchange medium such as quaternary aminoethyl (QAE) cellulose, diethylaminoethyl (DEAE) cellulose, or similar anion exchanger.

The chromatographic medium is washed with a buffered aqueous solution having an ionic strength sufficient to remove unbound protein but not AHF, i.e., 0–0.2 (0–0.2M sodium chloride, and the like). Finally the chromatographic medium is eluted with an aqueous solution having an ionic strength sufficient to elute AHF, i.e., about 0.2–0.6 (e.g. 0.2–0.6M sodium chloride, and the like) to give fractions containing AHF, which are then pooled.

The pooled fractions from the above chromatography contain Factor VIII:C having a specific activity of at least about 4000 AHF units per mg of protein and represent a substantially homogeneous preparation on ion exchange chromatography on QAE cellulose and sodium dodecyl sulfate (SDS) polyacrylamide gel electrophoresis (Laemmli). Such a product has heretofor, not been described, disclosed, or suggested by the prior art. The pooled fractions constitute Factor VIII:C purified at least about 350,000-fold over that found in plasma; it may be sterile filtered and lyophilized.

The pooled fractions from above may optionally be subjected to HPLC under non-denaturing conditions. For this purpose conventional HPLC apparatus may be employed and the elution of AHF accomplished in a standard manner based on Stokes' radius.

The fractions containing Factor VIII:C are pooled and represent a 10% yield of product; the Factor VIII:C has a specific activity of at least about 4,000 AHF units per mg of protein. The fraction may be sterile filtered and treated to reduce its water content either by ultrafiltration, lyophilization or combinations thereof. The Factor VIII:C preparation exhibits homogeneity by HPLC and SDS polyacrylamide gel electrophoresis (PAGE) (Laemmli). Thus, the Factor VIII:C preparation is essentially homogeneous and essentially free (i.e., contains less than about 1% combined of non-AHF proteins) of Factors II, VII, IX, X, fibrinogen, albumin, fibronectin, von Willebrand factor, and has essentially no activity in a non-activated partial thromboplastin time assay indicating that the purified protein essentially does not contain activated clotting factors circumventing the AHF dependent step in the clotting cascade.

The Factor VIII:C preparations of the invention, in addition to having the ability to correct the clotting defect in hemophilic plasma, also exhibit the following characteristics:

(a) The biological activity is increased, and the putative polypeptide chain is altered, following treatment with thrombin. The purified protein can be activated by treatment of thrombin to give 4–20 fold increase in AHF activity.

(b) The biological activity can be blocked by the inhibitors against AHF which are found in certain patients with classical hemophilia. When mixed with a several fold excess (unit:unit) of AHF inhibitor, between 95 and 99% of the measurable AHF activity can be abolished.

(c) The purified native Factor VIII:C, after reduction and SDS PAGE, appears a single polypeptide chain with an apparent molecular weight of about 100,000. Following incubation with thrombin, virtually all of the 100,000 polypeptide disappears and is replaced by bands with molecular weights of 75,000 and 26,000.

(d) The purified Factor VIII:C appears to be substantially free from significant protease activity, and from essentially all other plasma proteins.

(e) The purified Factor VIII:C is substantially free from AHF antigen (Factor VIII:C Ag). The ratio of AHF:AHF antigen is usually about 50:1 or greater, usually within the range of about 50:1–150:1.

The amino acid composition of the human AHF preparation of the invention is given in Table 1.

TABLE 1

| Human Factor VIII: C Amino Acid Composition | |
| --- | --- |
| Residue | % Total Amino Acids |
| Cysteic Acid | 2.62 |
| Aspartic Acid | 9.6 |
| Threonine | 3.65 |
| Serine | 5.49 |
| Glutamic Acid | 13.55 |
| Glycine | 10.5 |
| Alanine | 7.73 |
| Methionine | 2.44 |
| Isoleucine | 2.67 |
| Leucine | 11.65 |
| Tyrosine | 4.78 |
| Phenylalanine | 5.32 |
| Histidine | 3.01 |
| Lysine | 4.29 |
| Arginine | 8.90 |
| Valine | 3.75 |
| Cysteic Acid | 2.62 |

Tryptophan and Proline are not detected by the system the system used.
Cysteic acid is estimated from a performic acid oxidized sample.

Materials and Methods

Materials.

Parts and percentages are by weight unless otherwise specified. Concentrates obtained from human plasma cryoprecipitate were provided by Cutter Laboratories (Berkeley, Calif.) for purification of factor VIII. Hemophilic plasma was purchased from George King Bio-Medical, Inc. (Overland Park, Kans.). Radiolabeled Na$^{125}$I was obtained from New England Nuclear (Boston, Mass.), and radioiodination of factor VIII:C was performed using Enzymobeads™ which were purchased from Bio-Rad Laboratories (Richmond, Calif.). Human thrombin (4000 units/mg) and heparin were purchased from Sigma Chemical Co. (St. Louis, Mo.). Sephacryl S-300 and S-400 were purchased from Pharmacia Fine Chemicals (Piscataway, N.J.). The rabbits used for infusions were New Zealand Whites obtained from Hazelton Dutchland (Denver, Pa.) and weighed 2.5 to 4 kg.

Neuraminidase (Type VIII, 19 units/mg) was obtained from Sigma Chemical Co. (St. Louis, Mo.). Beta-galactosidase from *E. coli* (300 units/mg), alpha-mannosidase from jack bean (10 units/mg), and beta-N-acetyl-D-glucosaminidase from beef kidney (4 units/mg) were obtained from Boehringer Mannheim (Indianapolis, Ind.). Endoglycosidase D (endo-beta-N-acetylglucosaminidase D from *D. pneumoniae*, 20 units/mg) and Endoglycosidase H (endo-beta-N-acetylglucosaminidase H from *Streptomyces plicatus*, 31 units/mg) were generous gifts from Miles Laboratories, Inc. (Elkhart, Ind.). These glycosidases were essentially free of contaminating protease activity according to the manufacturer's specifications and had no effect on the electrophoretic mobility of bovine serum albumin after prolonged incubation at relevant concentrations.

Radioiodination of factor VIII.

Factor VIII:C (10 μg in 25 μl of imidazole-saline buffer) was radiolabeled with 1 mCi $^{125}$I using the Enzymobeads™ radioiodination reagent. Unreacted $^{125}$I was removed by gel filtration using Sephadex G-25. Bovine serum albumin (200 μg/ml) was added as a carrier to the labeled protein which was then extensively dialyzed against imidazole-saline buffer. When analyzed by NaDodSO$_4$ polyacrylamide gel electrophoresis and autoradiography, the iodinated factor VIII:C appeared as a single band of M$_r$ 100,000, indicating that it was not degraded. The specific activity of $^{125}$I-factor VIII:C was approximately 10$^6$ cpm/μg and was greater than 90% acid insoluble.

Glycosidase digestions.

As referred to in Example III, all reaction mixtures contained purified factor VII:C (200 μg/ml) or $^{125}$I-factor VIII:C (6–13 × 10$^6$ cpm) in imidazole buffered saline, those with labeled protein also including 200 μg/ml BSA in the buffer as a carrier. Reactions involving exoglycosidases contained neuraminidase (0.1 unit/ml, beta-galactosidase (0.1 unit/ml), alpha-mannosidase (0.05 units/ml) and N-acetyl glucosaminidase (0.1 unit/ml). Reactions with the exo- and endoglycosidases contained the above enzymes plus endoglycosidase D (0.02 units/ml) and endoglycosidase H (0.02 units/ml). Reaction volumes were 100 μl and all reactions were incubated at 37° C. for 18–22 hours. Glycosidase-treated, $^{125}$I-factor VIII was chromatographed on Sephacryl S-300 (1×20 cm), equilibrated in imidazole saline with 0.2% sodium azide and 500 μg/ml BSA and eluted in this buffer. Fractions (300 μl) were collected and monitored for radioactivity, and peak fraction(s) were dialyzed extensively into imidazole-saline prior to infusion into rabbits.

Thrombin-potentiated Activation.

Native and sugar-depleted factor VIII:C were assayed for thrombin-potentiated activation of clotting activity. Factor VIII:C was incubated with thrombin (10 units/ml) at 23° C. for 1 minute, and assayed using the one-stage assay. The decay of activity following activation was monitored from later time points (5 to 30 minutes) taken from similar reaction mixtures.

Clotting Assays.

AHF was measured by a one-stage clotting assay, using as substrate plasma from a patient with severe AHF deficiency (less than 1% AHF), and using a Fibrometer to determine the clotting time. One unit of AHF was defined as the amount in 1 ml of pooled normal human plasma. (Langdell et al, *J. Lab. Clin. Med.*, 41, 637-644, 1953.

Protein estimations were made using a Gilford 250 spectrophotometer. All samples were read at 280 nm and 320 nm, and the absorbance corrected for light scattering by the following formula.

$$A_{280\ corrected} = A_{280\ uncorrected} - 1.7\ (A_{320})$$

A mean $A_{280\ corrected}^{1\%}$ of 10.0 was assumed for calculations of specific activity.

Polyacrylamide gel electrophoresis.

Sodium dodecyl sulfate-polyacrylamide gel electrophoresis was performed according to O'Farrell employing a 4.5% stacking gel with an 8% or 6% separating gel. Electrophoresis was at 25 mA for four hours. Polyacrylamide gel electrophoresis under nondenaturing conditions employed a 5% gel and 25 mM Tris and 192 mM glycine, pH 8.3. Electrophoresis was at 250 volts for three hours at 4° C. (O'Farrell, *J. Biol. Chem.*, 250, 4007-4012 1975). Gels were stained for protein using silver nitrate and for carbohydrate using periodic acid Schiffs reagent. Protein was eluted from the unstained gel by slicing at 5 mm intervals and adding each slice to 0.3 ml of 50 mM Tris-hydrochloride, pH 7.0, 150 mM NaCl and 200 microgram/ml ovalbumin. The mixture was incubated at 4° C. for 2-3 hours and assayed for AHF procoagulant activity as described above.

Gels stained with PAS were scanned with a Quick Scan Jr. scanning densitometer (Helena Laboratories, Beaumont, Tex.) at 565 nm.

Factor VIII:C Ag Assay.

The procedure of Reisner et al was followed. The antibody was kindly provided by Howard Reisner. (Reisner et al, *Thromb. Research*, 14, 135-239, 1979).

Inhibition of AHF Activity.

This was measured by mixing 1 volume of sample containing AHF with an equal volume of human plasma containing inhibitor to AHF. The concentration of inhibitor was always several fold in excess of the AHF concentration. After incubation for the time indicated, the residual AHF was assayed.

Thrombin Activation of AHF.

(Switzer et al, *J. Biol. Chem.*, 255, 10606-10611, 1980).

von Willebrand Protein Assay.

(Voller et al, *Bull. World Health Organ.*, 53, 55-63, 1976).

Silver Stain.

(Merrill et al, *Science*, 211, 1437-1438, 1980).

EXAMPLE I

Purification of AHF

The starting material was AHF therapeutic concentrate (Koate®) from Cutter Laboratories, Inc.

(1) Referring to FIG. 1 gel permeation chromatography was carried out on Biogel A-15 m (Bio Rad Laboratories, 100-200 mesh) in a column 2.6×90 cm with CaCl$_2$ (1 mM), sodium citrate (5 mM), 0.135M NaCl, 5% dextrose, 0.1% sodium azide at pH 7.35 and at ambient temperature as the eluant. The fractions containing the highest concentrations of AHF were pooled (10) and concentrated by precipitation with 40% w/v ammonium sulfate. In preparation for the next step, the precipitate was dissolved in 50 mM imidazole buffer at pH 7.0 containing 150 mM NaCl and dialyzed to remove residual ammonium sulfate.

Figure 2:
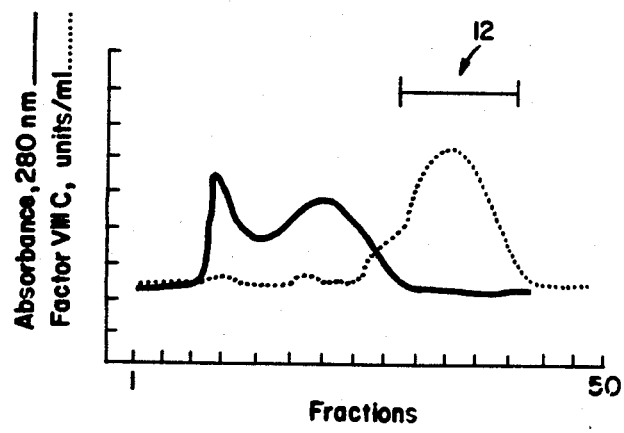

(2) The dialyzed sample from 1 above was made 250 mM in CaCl$_2$ by mixing 1 volume of 2.5M CaCl$_2$ with 9 volumes of protein solution. The sample was then chromatographed on a 2×100 cm glass column of Sepharose 4B-CL previously equilibrated with the same buffer. The elution medium was a 50 mM imidazole buffer at pH 7.0 containing 150 mM NaCl and 0.25M CaCl$_2$. Referring to FIG. 2, area 12 represents the fractions containing AHF activity, which were pooled.

Figure 3:
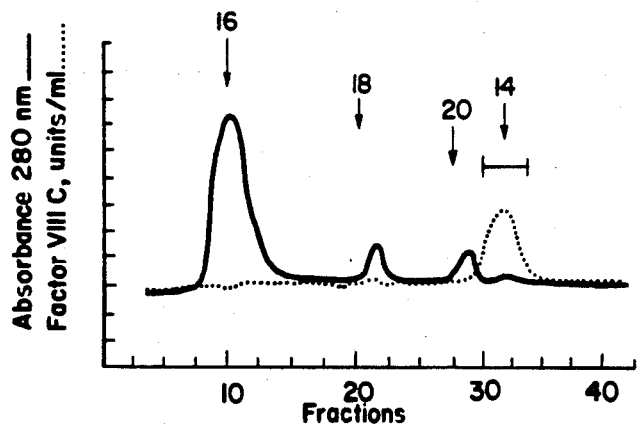

(3) The AHF pool (12) from the previous step was concentrated by placing the pool in a dialysis bag and immersing the bag in solid PEG-20,000. The concentrated sample was then dialyzed against 50 mM imidazole buffer pH 7.0 and 0.15 molar sodium chloride and was chromatographed on a 2.5×10 cm plastic column of QAE cellulose previously equilibrated with the same buffer. All of the AHF was bound under these conditions. Referring now to FIG. 3, when the unbound protein (16) had been washed through with 0.15M NaCl, a step gradient of 0.20M NaCl in the same buffer was run, an additional peak (18) of protein containing little or no AHF was eluted. Finally, a linear gradient of 180 ml from 0.20-1.0M NaCl was run at 17 ml per hour. An additional peak (20) of protein was eluted, and towards the end of this peak, the AHF activity eluted in a fairly sharp peak (14) starting at around 0.3M NaCl. The protein was pooled according to the AHF activity. Unbound proteins are indicated at 24 in FIG. 5 (SDS polyacrylamide gel electrophoresis [Laemmli] in a 6% gel); protein eluted with 0.2N NaCl is represented at 26; and the peak at 28 was eluted at 0.2M NaCl.

Figure 5:
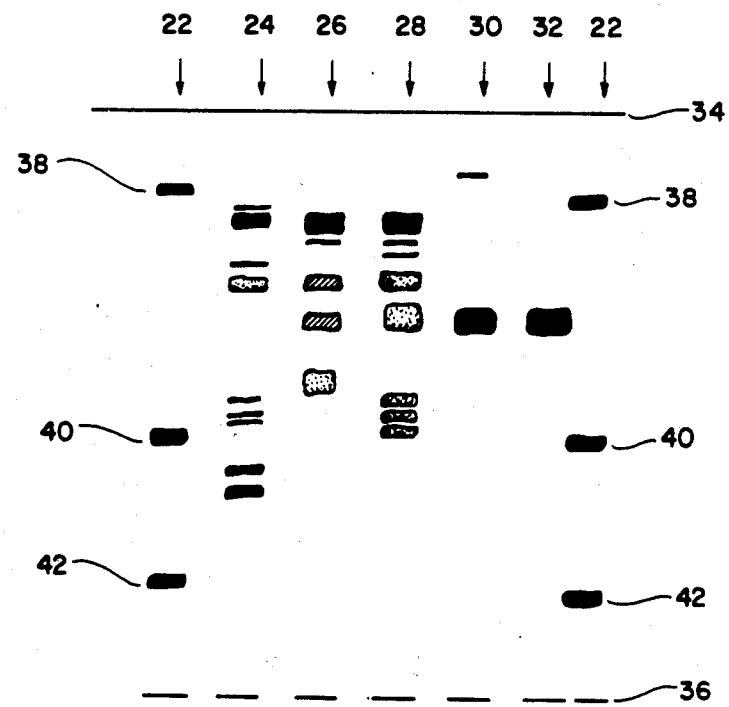
FIG. 5 is a depiction of the results of the SDS polyacrylamide gel electrophoresis (Laemmli, Nature, 277, 680–685, 1970, incorporated herein by reference) in a 6% gel on preparations produced in accordance with the invention.

The AHF preparation so-produced exhibited homogeneity (30) on SDS polyacrylamide gel electrophoresis (Laemmli) in a 6% gel (FIG. 5). The specific activity of this preparation was about 5,000 units of AHF activity per mg of protein, representing a 350,000 fold purification over source plasma. A 10% overall recovery from the commercial AHF concentrate was realized.

Figure 4:
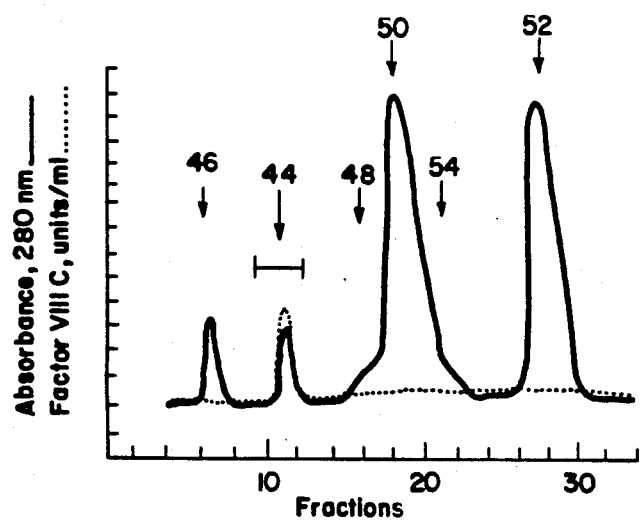

(4) The pooled fraction from step (3) was concentrated prior to high performance liquid chromatography (HPLC). HPLC was carried out on a Beckman TSK 4000 1×30 cm column at 40 psi, flow rate of 0.5 ml/minute. The profile is shown in FIG. 4. The AHF eluted coincident with the second peak (44), intermediate between the elution positions of IgM (MW 890,000) and IgG (MW 160,000). The two largest peaks 50 and 52 do not contain AHF activity and represent PEG (50) buffer and a change (52). Peak 54 represents *bovine serum albumin* (BSA). In FIG. 4, arrows at 46, 48, and 54 represent elution volumes of marker proteins of known molecular weights in parallel runs: 46=IgM (MW 890,000) and 48=IgG (MW 160,000).

Highly purified Factor VIII:C, according to the present invention, may also be purified by a modification of the procedure of the inventors as published in *P.N.A.S.* 72, 7200-7204 (1982). The partially purified factor VIII obtained from Sepharose 4B chromatography in 20 mM imidazole-Cl pH 7.0, 150 mM NaCl, 250 mM CaCl₂ 100 mM lysine-chloride and 0.02% sodium azide (as in Step 2 above) may be concentrated 20-fold in an Amicon ultrafiltration cell using a YM 10 membrane at 50 psi. The concentrated sample may then be applied to a 1.5×80 cm column containing Sephacryl S-400 equilibrated in the above buffer. This procedure would replace the QAE cellulose chromatography as the final purification step.

Referring to FIG. 5, the AHF pool from step 4 above is essentially homogeneous (32) on SDS PAGE (Laemmli) in a 6% gel. This preparation has a specific activity of about 5000 AHF units per mg of protein representing a purification factor of 350,000 over source plasma. In FIG. 5 the origin for the SDS PAGE is represented at 34 and the ion front at 36. Column 22 represents myosin heavy chain (38) molecular weight 200,000, BSA (40) molecular weight 68,000, and ovalbumin (42) molecular weight 43,000.

The above operations and results are summarized in Table 2.

TABLE 2

| | PURIFICATION OF HUMAN AHF | | | | | |
|---|---|---|---|---|---|---|
| | Volume (ml) | Total Protein (mg) | Total Activity (units) | Specific Activity (units/mg) | Yield (%) | Purification (x-fold) |
| Plasma | — | — | — | 0.014 | — | 1 |
| Koate | 250 | 12,580 | 11,000 | 0.87 | 100 | 62 |
| Biogel A-15 M ammonium sulfate dialysis | 22 | 318 | 9,469 | 29.8 | 86 | 2,126 |
| Ca⁺⁺ dissociation Sepharose CL-4B dialysis | 110 | 13.2 | 6,850 | 519 | 62 | 37,067 |
| QAE cellulose | 29.5 | 0.28 | 1,396 | 4,986 | 12.7 | 356,122 |

All values represent the average of two preparations.

EXAMPLE II

Preparation of Deglycosylated F. VIII:C and Electrophoresis with PAS Stain

Highly purified F. VIII:C prepared according to Example I was treated with exoglycosidases (which remove carbohydrates from a terminal and to a branch in the COOH chain) and endoglycosidases (which remove carbohydrates proximally of chain branching), as described under Materials and Methods.

Removal of carbohydrates was determined by electrophoresis in an 8% denaturing, polyacrylamide gel. After electrophoresis, the gel was stained for carbohydrate using periodic acid - Schiffs reagent (PAS). This staining procedure allows for the determination of relative amounts of carbohydrate in the protein by comparing the intensities of the stain, as determined by scanning densitometry.

The untreated F. VIII:C and the exoglycosidase treated F. VIII:C showed similar intensity of staining and similar areas under the scanning densitometer curves. This indicates that very little, (less than 10%) sugar is removed by the exoglycosidase mixture alone. The F. VIII:C plus exo- and endoglycosidases showed significantly diminished staining intensity. The area under the scanning densitometer curve for this material indicated that about 50% of the total carbohydrate was removed from Factor VIII:C when treated with the combination of exo- plus endoglycosidases to produce F. VIII:C having substantially lowered carbohydrate content compared to native F. VIII:C, i.e. "deglycosylated" F. VIII:C.

Figure 6:
FIG. 6 is a photographic representation of PAS-stained F. VIII:C treated with various glycosidases.

The deglycosylated F. VIII:C consisted of a single polypeptide with an increased rate of mobility on the SDS/PAGE equivalent to a new $M_r$ of 95,000, compared to an $M_r$ of 100,000 $M_r$ for untreated F. VIII:C. The F. VIII:C treated solely with exoglycosidases showed an approximate $M_r$ of 97,000. FIG. 6 represents a PAS stained gel showing in lane 1 exo- and endoglycosylate-treated (deglycosylated) F. VIII:C, in lane 2 untreated F. VIII:C, and in lane 3 exoglycosidase-treated F. VIII:C. Lane 1 shows the decreased PAS stain of the deglycosylated F. VIII:C compared to the material of both lane and lane 3.

EXAMPLE III

Figure 7:
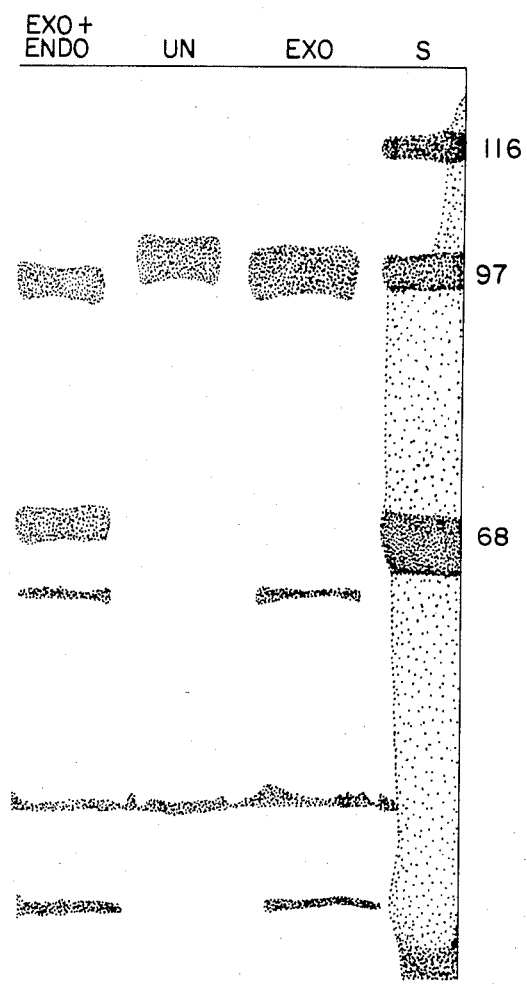
FIG. 7 is a photograph showing SDS polyacrylamide gel electrophoresis of deglycosylated (glycosidase-treated) F. VIII:C.

Preparation of Deglycosylated F. VIII:C - Further Electrophoresis with Silver Nitrate Stain Referring now to FIG. 7, F. VIII:C was treated with (1) exoglycosidases and a (2) combination of endoglycosidases and exoglycosidases for 18–24 hours at 37° C. prior to electrophoresis using a 8% separating SDS-polyacrylamide gel as described in Materials and Methods, above. Following electrophoresis, the gel was stained with silver nitrate. The electrophoretic mobility of Factor VIII (lane 2) was increased following treatment with the exoglycosidases (lane 3) resulting in a new $M_r$ of 97,000.

Treatment with the combination of exoglycosidases and endoglycosidases resulted in a further reduction in size, lane 1, showing an $M_r$ of 95,000. The band at 68,000 in lane 1 is bovine serum albumin (BSA) present in the endoglycosidases as a stabilizing agent. Lane 4 represents high molecular weight protein standards; the numbers to the right represent the size of these standards and are expressed as $M_r \times 10^{-3}$.

The Factor VIII:C (Mr 100,000) is cleaved by thrombin into two fragments of $M_r$ 75,000 and 26,000. $^{125}$I-labeled Factor VIII was treated with the exoglycosidase cocktail following thrombin cleavage of Factor VIII. The reaction mixtures were subjected to 10% SDS-polyacrylamide gel electrophoresis followed by autoradiography. Factor VIII:C treated with thrombin yielded the $M_r$ 75,000 and ~26,000 polypeptides. After thrombin treatment, the F. VIII:C was treated with the exoglycosidase cocktail. The $M_r$ 75,000 polypeptide is not significantly changed in electrophoretic mobility while the $M_r \sim 26,000$ polypeptide shows a significant increase in electrophoretic mobility suggesting that this polypeptide is relatively rich in carbohydrate (at least sialic acid) relative to the $M_r$ 75,000 polypeptide.

Activation by thrombin and quantification of sugar removal are set forth in Table 3.

TABLE 3

| Condition | % Sugar Remaining (±SD) | % Activity (±SD) | Thrombin Activation (x-fold) |
|---|---|---|---|
| Factor VIII | 100 | 100 | 24 |
| +Exoglycosidase | 87 ± 6 | 119 ± 24 | 21 |
| +Exo-plus endoglycosidase | 54 ± 4 | 91 ± 18 | 20 |

The percent sugar remaining indicates the amount of PAS stainable material, following NaDodSo4 polyacrylamide gel electrophoresis, determined by scanning densitometry. Values represent the average (with standard deviation) of three separate determinations. Percent activity values are the average (with standard deviation) of four separate experiments. Thrombin activation values represent the ratio of units of thrombin-activated factor VIII to units of unactivated factor VIII.

While some variability was observed, no significant increase or decrease in clotting activity was observed relative to the untreated Factor VIII.

The clotting activity was determined according to the assay set forth above.

EXAMPLE V

In Vivo Survival of Deglycosylated Factor VIII:C

Purified Factor VIII:C was trace labelled with $^{125}I$ using lactoperoxidase and glucose oxidase coupled to insoluble beads. The labelled protein was separated from non-covalently bound iodine using gel filtration followed by dialysis. Factor VIII labelled by this procedure retains 5–10% of its clotting activity and migrates in a reduced SDS PAGE in a single polypeptide chain $M_r$ 100,000 with the same electrophoretic properties as its unlabelled counterpart.

Approximately 50–100 ng of labelled Factor VIII (6–13 × 10$^6$ cpm) were injected carefully into the central ear vein of a 2 kg New Zealand white rabbit. Samples of blood were withdrawn after different time intervals, from an indwelling scalp vein needle in the opposite ear. Samples of 1 ml were removed, mixed with 1/100 volume of 40% citrate, and counted in a gamma counter. The amount of labelled protein remaining was plotted against time, in order to determine the rate of clearance of labelled protein.

Several samples of plasma from different times after infusion were analyzed by SDS PAGE. The results confirm that the radioactivity continues to be associated covalently with the protein.

The results of 3 separate experiments in 2 animals indicate that about 50% of the labelled protein (either native or deglycosylated) disappears with a half time of ~60 minutes, whereas most of the remainder continues to circulate with a half time of about 4 hours. Although not shown in FIG. 8, we have found that a small fraction of the Factor VIII, perhaps ~20%, appears to have an even longer half life, in the range of 10–12 hours.

A similar infusion experiment was carried out with Factor VIII which was treated for 15 hours with neuraminidase to remove terminal sialic acids. This treatment has been shown to have no effect on the clotting activity of Factor VIII in vitro, and to cause a small increase in the rate of migration of Factor VIII in SDS PAGE.

When the desialylated Factor VIII was infused intravenously, about 90% of the activity disappeared from the plasma within 5 minutes of infusion. The remaining 10% remained in circulation with a biological half time of ~4-5 hours. The results with the desialylated Factor VIII are similar to those seen with many other (but not all) plasma glycoproteins. Removal of the terminal sialic acids results in the very rapid clearance from the plasma of a major fraction of the protein. This effect on clearance time is in contrast to the lack of detectable effect on clotting activity in vitro, as reported earlier.

Figure 8:
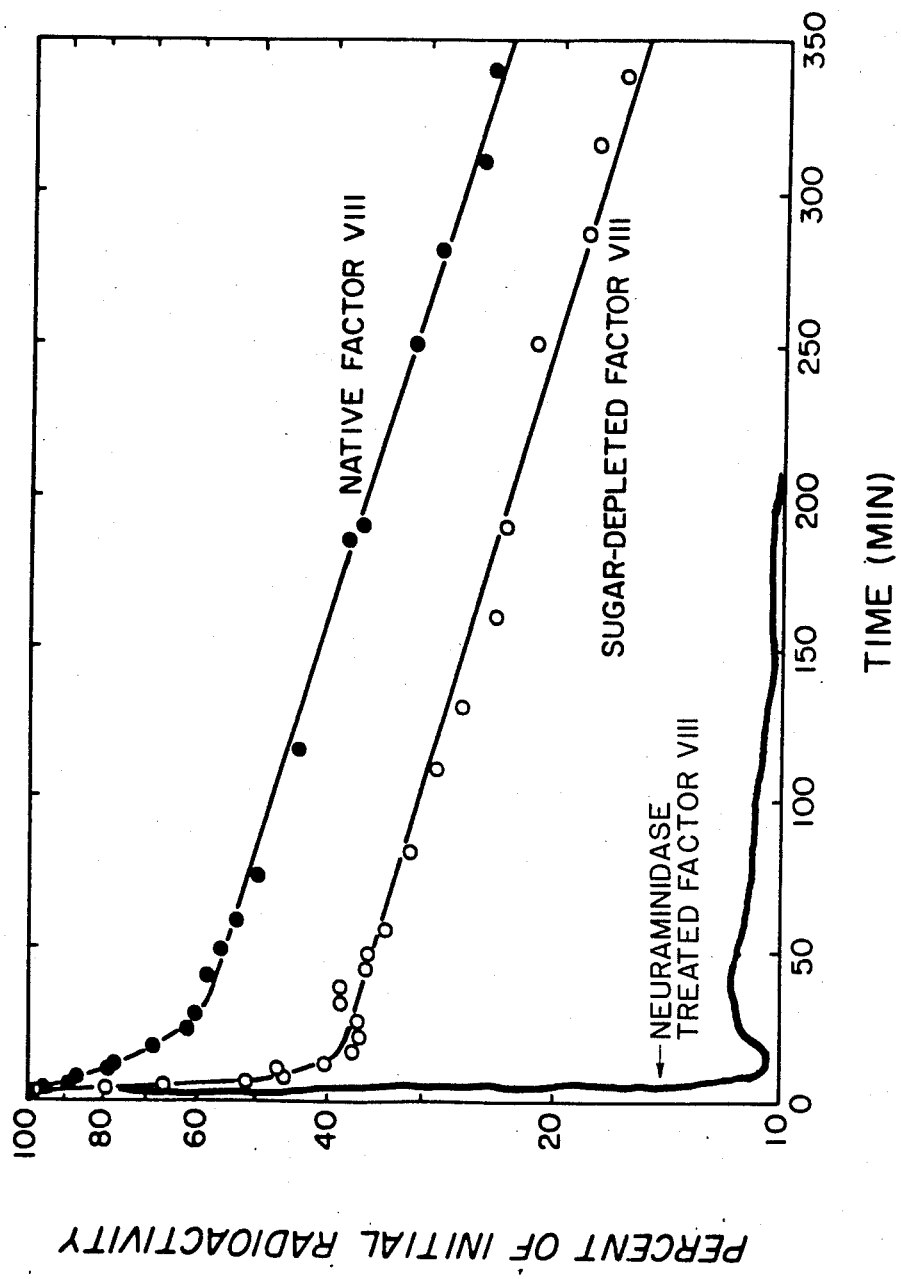
FIG. 8 is a chart showing in vivo survival times of the deglycosylated (glycosidase-treated) F. VIII:C.

Referring now to FIG. 8, the closed circles indicate the survival of native $^{125}I$-factor VIII:C Open circles indicate the survival of deglycosylated $^{125}I$-factor VIII:C. The lowest line shows survival of neuraminidase-treated F. VIII:C is shown to indicate the rapid clearance of this material, as discussed above. The 100% point was obtained immediately after infusion (<30S) and was in agreement with the calculated value based upon blood volume and dose. The half-life of survival was determined from the linear portion of the curves which followed the initial, rapid clearance phase.

Both native highly purified F. VIII:C and the deglycosylated F. VIII:C showed a 2-phase decay curve with a rapid initial phase followed by a slow metabolic decay. Untreated material showed a drop in radioactivity to 60% of initial within 25 minutes; sugar-depleted protein decreased to 40% in 15 minutes. Following the rapid clearance rates, both types of factor VIII proteins were cleared from the circulation at similar rates with a half-life of about 250 minutes (4–5 hours).

What is claimed is:

1. A highly purified protein material having F. VIII:C procoagulant activity, free of mature F. VIII:vWF and other procoagulant activities, characterized in that it contains less than 7%–5% by weight of carbohydrate associated therewith, further characterized by an $M_r$ on SDS/PAGE of about 95,000, having F. VIII:C activity of at least 4,000 AHF units per mg protein and further characterized in that activation of said material by thrombin produces two fragments having an $M_r$ of about 75,000 and the other an $M_r$ about 26,000.

2. A method of treatment of classic Hemophilia (Factor VIII deficiency) comprising administration of the material of claim 1 in an effective amount to a patient in need of such treatment.

* * * * *